(12) United States Patent
Weiss et al.

(10) Patent No.: US 6,510,724 B1
(45) Date of Patent: Jan. 28, 2003

(54) METHOD AND SYSTEM FOR SELECTIVE SOLDERING PROCESS CHARACTERIZATION

(75) Inventors: Mark Weiss, Scottsdale, AZ (US); Peter Gibson Goolsby, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 355 days.

(21) Appl. No.: 09/613,149

(22) Filed: Jun. 8, 2000

(51) Int. Cl.[7] ............................................. G01N 19/00
(52) U.S. Cl. ........................................ 73/1.01; 73/865.9
(58) Field of Search .............................. 73/866.4, 865.9, 73/1.01

(56) References Cited

U.S. PATENT DOCUMENTS

| | | | |
|---|---|---|---|
| 4,040,078 A | * 8/1977 | Eckton, Jr. et al. ........... | 357/30 |
| 4,636,073 A | * 1/1987 | Williams ..................... | 356/243 |
| 5,023,848 A | 6/1991 | Frey et al. .................... | 368/1 |
| 5,388,468 A | 2/1995 | Sasson ....................... | 73/865.9 |
| 5,558,541 A | * 9/1996 | Botka et al. ................. | 439/675 |
| 5,767,424 A | * 6/1998 | Breunsbach et al. ........ | 73/865.9 |
| 6,119,915 A | * 9/2000 | Thompson, Sr. ............. | 228/37 |

* cited by examiner

*Primary Examiner*—Daniel S. Larkin
*Assistant Examiner*—Nashmiya Fayyaz
(74) *Attorney, Agent, or Firm*—Kevin D. Wills

(57) ABSTRACT

In a selective soldering machine (FIG. 1, 5), a calibration circuit board (FIG. 2, 100) makes contact with a solder wave (FIG. 1, 25). The calibration circuit board (100) is interfaced with a desktop computer unit (FIG. 4, 160) through a optoisolator unit (FIG. 4, 150). The desktop computer unit (160) records which of the contact points (FIG. 2, 120) distributed on the calibration circuit board (100) come into contact with the solder wave (25). This data is then used to establish the solder contact area (FIG. 6, 129) as a function of the various parameters of the selective soldering machine (5). These parameters include the flow rate and flow pressure of solder from the solder pot, the angle of inclination of the electronics board (FIG. 1, 30), the speed of the solder pump (12), the distance from the leads (39) to the solder wave (25), the motion vector which a gantry (50) applies to the electronics board (30), and any preheating which may be applied the electronics board (30).

15 Claims, 2 Drawing Sheets

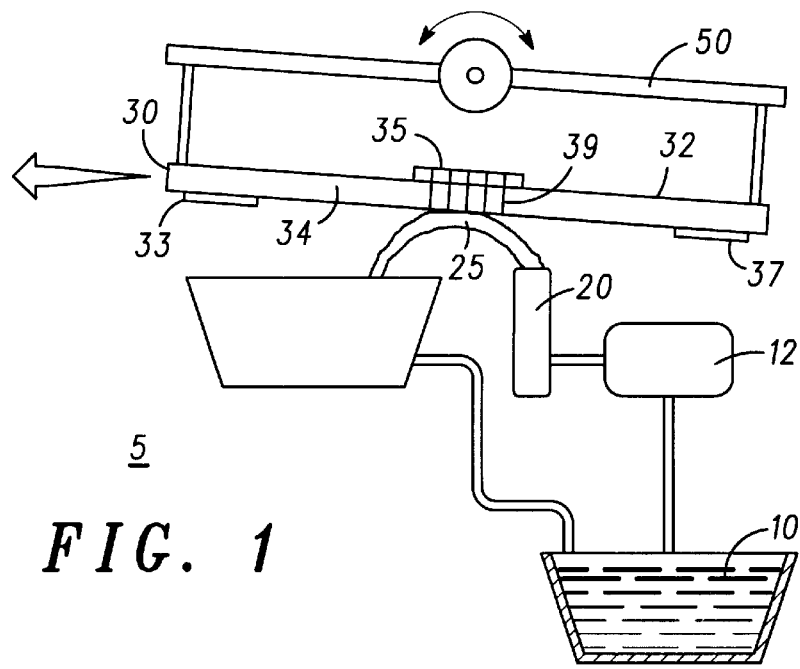
FIG. 1
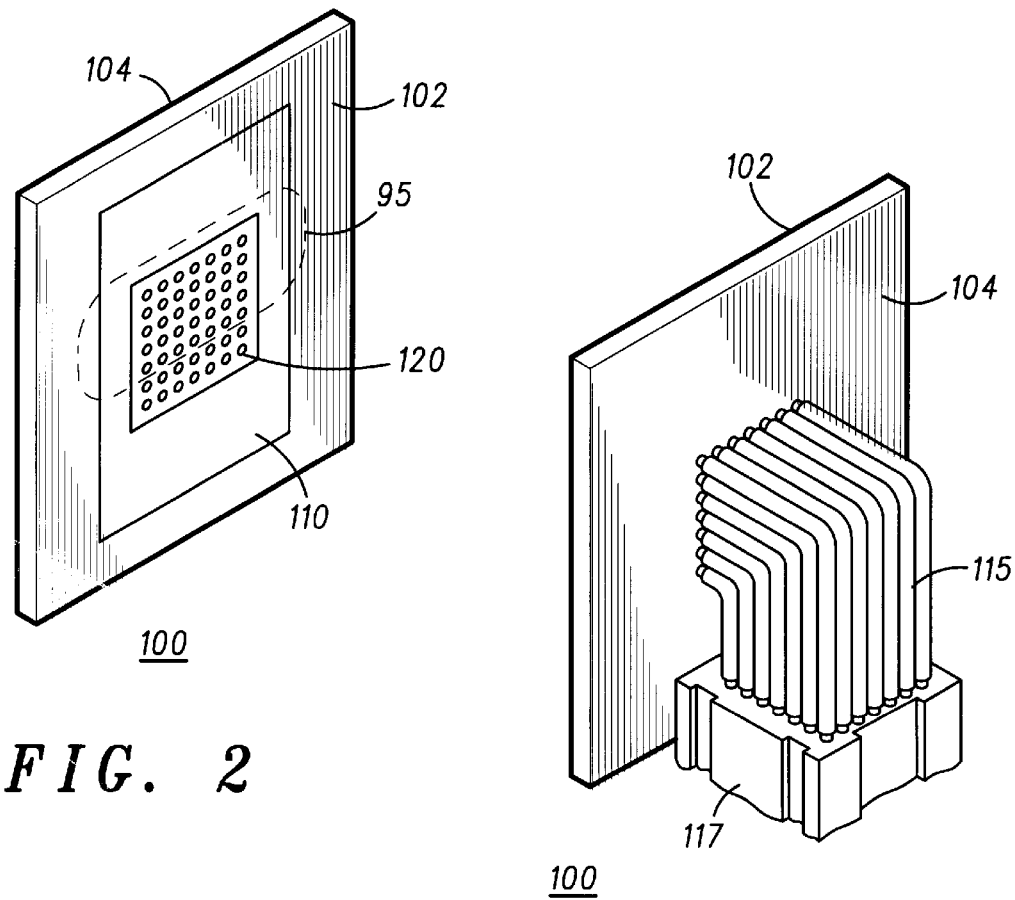
FIG. 2
FIG. 3

METHOD AND SYSTEM FOR SELECTIVE SOLDERING PROCESS CHARACTERIZATION

FIELD OF THE INVENTION

The invention relates to the field of electronics manufacturing and, more particularly, to techniques for selective soldering process characterization.

BACKGROUND OF THE INVENTION

In an automated electronics manufacturing environment, wave solder machines are used in order to reliably solder electronics components onto electronic circuit boards. In such an environment, components are affixed to a top surface of an electronics board while the component leads extend through the board to a second side. This board is then placed within a selective soldering machine and drawn over the surface of a wave of molten solder which extends over the entire width of the electronics board. Through the action of moving the electronics board across a solder wave, the components affixed to a top surface of the electronics board are soldered into place.

When an electronics board incorporates components which are affixed to both a top and a bottom surface of the electronics board, a solder wave which extends the width of the board cannot be used in order to solder components into place, since the solder wave will invariably come into contact with components located on the side of the board to which solder is being applied. Thus, a selective soldering machine is used in order to facilitate the soldering of components located at selected areas of an electronics board with components present on both sides.

In a selective soldering machine, a much smaller solder wave is used to solder electronics components to specific areas of the electronics board. In a selective soldering machine, a solder wave can be generated that measures only a fraction of an inch in both length and width. A computer-controlled gantry is then used to bring very specific areas of the electronics board into contact with the smaller solder wave. However, this process can still result in exposing undesired locations of the electronics board to the solder source. This results in degrading pre-existing solder contacts, as well as causing damage to electronics components which unintentionally make contact with the solder source. These can result in the electronics components becoming detached from the electronics board, as well as degrading the integrity of pre-existing solder bonds.

Therefore, it is highly desirable to make use of a method and system for selective soldering process characterization. This would allow electronics manufacturers to impose a greater degree of precision on the selective soldering process and thus reduce the incidences of components becoming detached from an electronics board, as well as maintaining the integrity of pre-existing solder bonds which are adjacent to the solder sources.

BRIEF DESCRIPTION OF THE DRAWINGS

The invention is pointed out with particularity in the appended claims. However, a more complete understanding of the present invention may be derived by referring to the detailed description and claims when considered in connection with the figures, wherein like reference numbers refer to similar items throughout the figures, and:

FIG. 1 illustrates an environment which includes the functional elements of a selective soldering machine (5) with which a preferred embodiment of the invention may be practiced.;

FIG. 2 is an isometric view of a calibration circuit board used in characterizing an automated soldering process in accordance with a preferred embodiment of the invention;

FIG. 3 is another isometric view of a calibration circuit board for use in characterizing an automated soldering process in accordance with a preferred embodiment of the invention;

DESCRIPTION OF THE PREFERRED EMBODIMENTS

Figure 4:
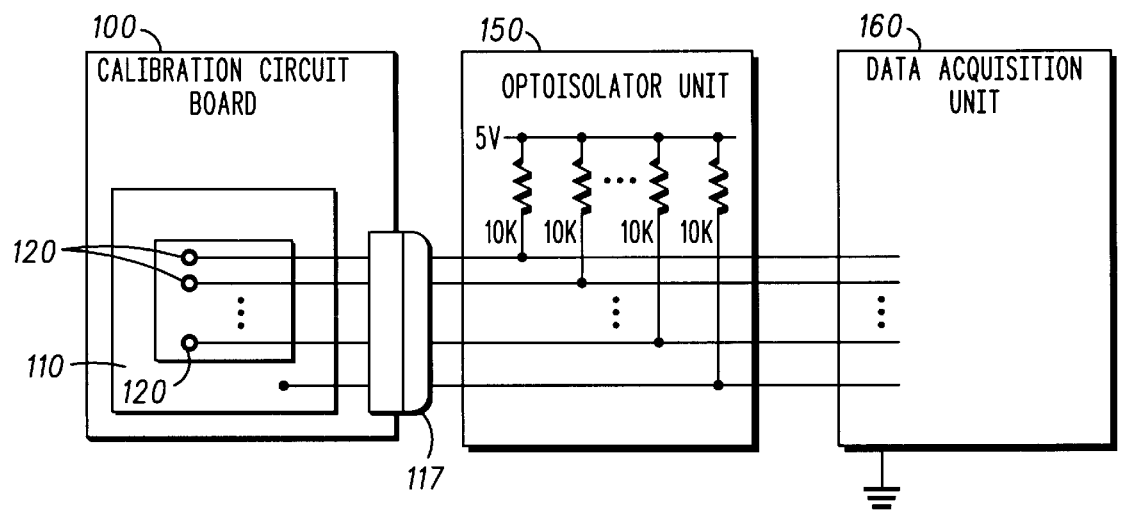
FIG. 4 is a block diagram of the logical elements of a system for selective soldering process characterization in accordance with a preferred embodiment of the invention.

A method and system for selective soldering process characterization provides a technique for more tightly controlling the selective soldering process performed by a selective soldering machine. When deployed in a high-volume manufacturing environment, the use of the method and system provide a means for reducing the number of defects caused by improper soldering as well as increasing the yield of electronic circuit boards produced by way of a selective soldering machine.

FIG. 1 illustrates an environment which includes the functional elements of a selective soldering machine (5) with which a preferred embodiment of the invention may be practiced. In FIG. 1, solder pot 10 functions as a reservoir for the molten solder which is used in the selective soldering machine. Solder pump 12 serves to remove solder from solder pot 10 and convey the solder to solder source 20. Desirably, solder source 20 incorporates a nozzle or other means for generating solder wave 25 which brings the solder into contact with leads 39 of electronics board 30. In a preferred embodiment, leads 39 extend through electronics board 30 from first side 32 to second side 34 of electronics board 30.

Desirably, second side 34 of electronics board 30 includes various circuit paths which allow component 35 to function within the circuit environment of electronics board 30. By way of example, and not by way of limitation, surface mount components 33 and 37 are adjacent to leads 39 and represent additional components on second side 34 of electronics board 30.

FIG. 1 also includes gantry 50 which represents a means for bringing a solder source into contact with a circuit board oriented in a horizontal plane in order to bring leads 39 into contact with the solder source. Gantry 50 provides the capability to move electronics board 30 in a horizontal plane and preferably enables motion in other directions such as providing a change in the angle of incline (or contact angle) of electronics board 30. FIG. 1 further includes means for moving electronics board 30 along a roll axis, or a yaw axis by way of gantry 50 or other means. Through the use of gantry 50, electronics board 30 can be judiciously placed into contact with solder wave 25, allowing solder to be applied to leads 39 in a precise manner.

Preferably, gantry 50 includes a stepper motor which facilitates the precise movement of electronics board 30. In an alternate embodiment, gantry 50 is implemented using a servomotor which precisely controls the positioning of electronics board 30. In either embodiment, gantry 50 can either momentarily hold electronics board 30 in place while leads 39 make contact with solder wave 25, or may apply a motion vector to electronics board 30 so that the board is constantly moving relative to solder wave 25. In this case, each of leads 39 is drawn over solder wave 25 as opposed to merely being placed into momentary contact with the solder wave.

Desirably, solder pump 12 includes the necessary control means to provide a constant flow rate and flow pressure of solder from solder pot 10 regardless of the fill level of the solder in solder pot 10. This allows the characteristics of solder wave 25 to be largely independent of the amount of solder in solder pot 10. However, the present invention is not limited to the use of selective soldering machines which employ this type of control logic. Thus, solder pump 12 need not incorporate these control means in order for the invention to be practiced. Other variables which can affect the solderability of leads 39 on electronics board 30 include the angle of inclination (or contact angle) of electronics board 30, the speed of solder pump 12, the distance of leads 39 to solder wave 25, the motion vector which gantry 50 applies to electronics board 30, and any preheating which may be applied to electronics board 30.

In an alternate embodiment, gantry 50 of FIG. 1 may function to hold electronics board 30 stationary while solder wave 25 is moved relative to the electronics board. This can also include moving one or more of solder source 20, solder pump 12, or solder pot 10 in cooperation with the motion of solder wave 25. In this embodiment, FIG. 1 includes means for bringing a solder source, such as solder wave 25, into contact with calibration circuit board 100.

FIG. 2 is an isometric view of a calibration circuit board used in a method and system for characterizing a selective soldering process in accordance with a preferred embodiment of the invention., In FIG. 2, calibration circuit board 100 includes first side 102, second side 104, trigger area 110, and contact points 120. Calibration circuit board 100 represents a predominantly planar and substantially rigid electronics board similar to electronics board 30 with the exception that calibration circuit board 100 includes means for indicating that a solder source has made contact with a particular location in a horizontal plane of calibration circuit board 100.

In a preferred embodiment, calibration circuit board 100 is inserted into the selective soldering machine 5 of FIG. 1 in place of electronics board 30. Desirably, calibration circuit board 100 is positioned with first side 102 being exposed to solder wave 25 of FIG. 1. Calibration circuit board 100 then functions to assist in determining which of contact points 120 come into contact with solder wave 25 according the various machine parameters as discussed in reference to FIG. 1.

In a preferred embodiment, calibration circuit board 100 is constructed using an insulating material, such as FRA, or a suitable ceramic material.

Generally, the material selection for calibration circuit board to 100 is driven by the desired spacing between each of contact points 120. It is generally anticipated that a more rigid material, such as a ceramic, can support closer spacing between each of contact points 120 than would be possible when using a less rigid or softer material, such as FR4.

Although contact points 120 of FIG. 2 are shown as being arranged in a rectangular grid pattern, this distribution pattern is not essential to practicing the invention. Therefore, contact points 120 can be arranged in a pattern that resembles a crosshair ("+"), an "X", or other suitable pattern such as parallel vertical lines crossing two parallel horizontal lines (tic-tac-toe pattern). Additionally, nothing prevents the use of contact points 120 arranged at irregular intervals, where non-uniform spacing between each of contact points 120 is used.

Each of contact points 120 includes a conductive annular ring which surrounds a center conductor. Desirably, the center conductor is fed through calibration circuit board 100 from second side 104 to first side 102. Further details relative to the design and construction of contact points 120, as well as the actual spacing and construction of each of contact points 120, are described in further detail in the discussion of FIG. 5, herein.

FIG. 3 is another isometric view of a calibration circuit board for use in characterizing an automated soldering process in accordance with a preferred embodiment of the invention. In FIG. 3, indications that one or more of contact points 120 has come into contact with solder wave 25 are conveyed through each of signal lines 1 15. Each of signal lines 115 is terminated at connector 117 for transmission to external equipment. Thus, the calibration circuit board of FIGS. 2 and 3 provides a means for conveying, to external equipment, those of contact points 120 which have come into electrical contact with solder wave 25.

In a preferred embodiment, each of contact points 120 is constructed using a substantially non-solderable material, such as nickel or molybednum. Therefore, each of contact points 120 can come into contact with solder wave 25 of FIG. 1 without the solder adhering to the contact point. This allows calibration circuit board 100 to be used repeatedly in order to provide repeated independent measurements.

In FIG. 2, trigger area 110 is a conductive region which surrounds the arrangement of contact points 120. In a preferred embodiment, trigger area 110 is also constructed using a substantially non-solderable material, such as nickel or molybednum. This allows the external recording means, such as that described in reference to FIG. 4, herein, to begin recording only after trigger area 110 is placed in contact with solder wave 25 of FIG. 1.

For a variety of applications, it is anticipated that solder wave 25 of FIG. 1 will encompass an area which is significantly larger than the area encompassed by contact points 120. In FIG. 2, solder contact area 95 represents a typical area of solder contact on calibration circuit board 100, although this exemplary relative size and shape of the solder contact area are not intended to be limiting in any manner, and the invention may be practiced using solder sources which produce larger or smaller relative solder contact areas. Thus, it is likely that when solder wave 25 of FIG. 1 makes contact with one or more of contact points 120, the solder wave will likely also make contact with trigger area 110, thereby allowing trigger area 110 to function as an indicator to external equipment to begin recording the status of contact points 120 based on the status of trigger area 110.

FIG. 4 is a block diagram of the logical elements of a system for selective soldering process characterization in accordance with a preferred embodiment of the invention. In FIG. 4, contact points 120 are distributed horizontally and vertically across the surface of calibration circuit board 100.

Optoisolator unit 150 serves to provide a nominal voltage, such as 5 Volts, in order to provide an electrical potential to each of contact points 120. Desirably, a current limiting resistor of a nominal value, such as 10 KiloOhm, is provided between the voltage source of optoisolator unit 150 and each of contact points 120. Optoisolator unit 150 also serves to provide a level of circuit isolation between calibration circuit board 100 and data acquisition computer 160 to ensure that stray voltages from the circuit board do not cause damage to sensitive electronics operating within the data acquisition computer.

In a preferred embodiment, solder wave 25 of FIG. 1 is electrically connected to a system ground. Desirably, this ground is electrically similar to the ground of desktop computer unit 160. Thus, when each of contact points 120 comes into contact with solder wave 25, the voltage potential of the affected contact point is reduced from 5 Volts to a value which approximates 0 Volts relative to system ground. This change in voltage of each of contact points 120 is conveyed through connector 117 and recorded by way of desktop computer unit 160. In this manner, the electrical potential recorded by desktop computer unit 160 can be used as an indicator which provides information as to whether a particular one of contact points 120 has come into contact with solder wave 25.

Preferably, trigger area 110 functions in an electrically identical fashion as each of contact points 120. Thus, trigger area 110 is supplied with a voltage potential which drops to a nominal value when the trigger area contacts solder wave 25. However, the programming of desktop computer unit 160 desirably handles the input corresponding to trigger area 110 in a unique manner in that the computer unit does not begin recording signals from contact points 120 until the trigger area has contacted solder wave 25. Through the use of this triggering mechanism, desktop computer unit 160 begins data collection only after solder wave 25 contacts calibration circuit board 100.

It is important to point out that desktop computer unit 160 is representative of any type of programmable electronic device which has been adapted to include specialized hardware which can read signals from optoisolator unit 150 as well as store, retrieve, and process information pertinent to each signal. This allows the invention to be practiced by way of a specialized hand-held computer, or as one of many tasks executed by a larger computer system which possesses the required functionality. Further, it may be advantageous to employ an alternate triggering mechanism, other than trigger area 110, to indicate that calibration circuit board 1 00 has come into contact with solder wave 25. This triggering mechanism can be facilitated by way of a mechanical or optical means.

Figure 5:
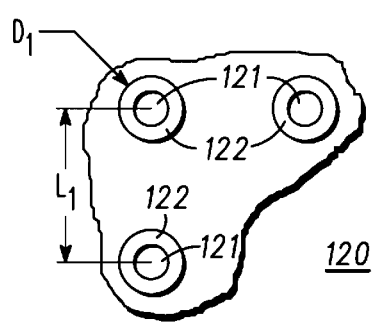
FIG. 5 it is an illustration of an arrangement of contact points distributed along a surface of the a calibration circuit board for use in a system for selective soldering process characterization in accordance with a preferred embodiment of the invention.

FIG. 5 is an illustration of the details of each of contact points 120 used in a system for selective soldering process characterization in accordance with a preferred embodiment of the invention. In FIG. 5, each of contact points 120 includes conductive annular ring 122 surrounding center conductor 121. Desirably, center conductor 121 is fed through calibration circuit board 100 from second side 104 to first side 102. The dimension "D1" represents the diameter of each of contact points 120, while the dimension "L1" represents the spacing between each of the contact points. As previously mentioned, it is expected that these dimensions are influenced by the choice of materials used in the construction of calibration circuit board 100. For softer materials such as FR-4, L1 is expected to be not less than 40 mils, with "D1" in the neighborhood of not less than 20 mils. However, when calibration circuit board 100 is constructed using a more rigid material, such as a ceramic, L2 may be as little as four mils, with D1 being as little as two mils.

In an alternate embodiment, each of contact points 120 is a substantially solid conductive pad. The use of such a contact pad is more in line with conventional practices when calibration circuit board 100 is constructed of a ceramic material. Additionally, although calibration circuit board 100 has been described herein as being constructed of a substantially rigid insulating material which includes conductive contact points 120, nothing prevents the use of a predominantly planar conductive material, such as aluminum or steel, to construct calibration circuit board 100. In this embodiment, conductive annular ring 122 is replaced by an insulating sleeve which surrounds a substantially non-solderable conductive material similar to center conductor 121. The use of an insulating sleeve to surround center conductor 121 provides electrical isolation between the center conductor and the surrounding predominantly conductive material.

Figure 6:
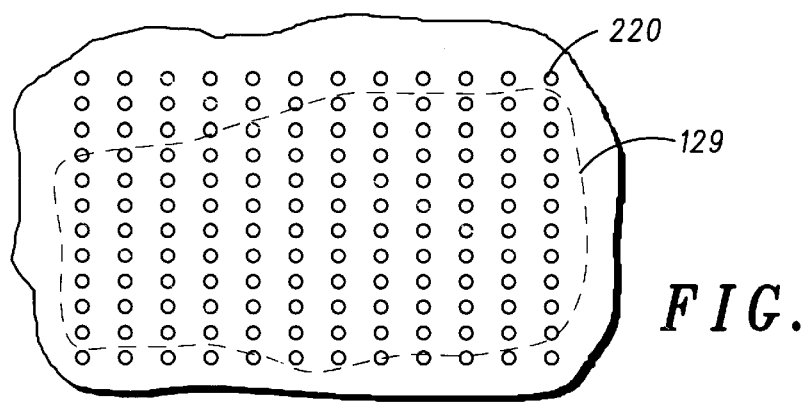
FIG. 6 is a graphical representation of an area occupied by a solder source relative to an arrangement of contact points located on a calibration circuit board in accordance with a preferred embodiment of the invention.

FIG. 6 is a graphical representation of an area occupied by a solder source relative to an arrangement of contact points located on a calibration circuit board in accordance with a preferred embodiment of the invention. In FIG. 6, an array of contact points 220 is placed proximate with a solder source, such as solder wave 25 of FIG. 1. The resulting contact area (129) can then be determined using indications from each of contact points 220. This data can then be used to generate Table 1 which identifies the number of contact points 220 which fall within solder contact area 129. Each row of Table 1 corresponds to a row of contact points 220, and indicates the number of contact points which fall within solder contact area 129. From FIG. 6 it can be seen that none of the top row of contact points 220 falls within solder contact area 129. For this reason, the Number of Contacts of Table 1 includes a "0" in row 1. Also from FIG. 6, it can be seen that 7 of contact points 220 make contact with solder contact area 129. Thus, the Number of Contacts of Table 1 includes a "7" in row 2. Similarly, 9 of 220 in row 3 fall within solder contact area 129, thus the necessitating an entry of "9" in row 3 of Table 1. Since each of contact points 220 in rows 4-11 of FIG. 6 falls within solder contact area 129, the corresponding rows of Table 1 include a "12" in the Number of Contacts field. Finally, in a row 12 of FIG. 6, 6 of contact points 220 fall within solder contact area 129, thus requiring an "6" in the Number of Contacts for row 12 of Table 1.

TABLE 1

| Row Number versus Contacts with Solder Source | |
|---|---|
| Row Number | Number of Contacts |
| 1 | 0 |
| 2 | 7 |
| 3 | 9 |
| 4 | 12 |
| 5 | 12 |
| 6 | 12 |
| 7 | 12 |
| 8 | 12 |
| 9 | 12 |
| 10 | 12 |
| 11 | 12 |
| 12 | 6 |

Through the use of Table 1, a precise representation of solder contact area 129 can be determined. Other types of representations, such as histograms and bar graphs are also possible. Each of these representations can then be correlated to actual distances on an electronics circuit board, such as electronics board 30 of FIG. 1. By way of this correlation, a keep-out region on the electronics board can be established. To the outside of the keep out region, electronics components can be placed without concern that the components will be damaged by contacting a solder source. Within the keep out region, electronics components would likely come into contact the solder source.

A table similar to Table 1 can be generated in order to characterize a selective soldering machine, such as that of FIG. 1, as a function of a variety of machine parameters. These parameters include, but are not necessarily limited to: the flow rate and flow pressure of solder from the solder pot, the angle of inclination (contact angle) of the electronics board, the speed of the solder pump, the distance from electrical leads to the solder wave, and the motion vector which a gantry applies to the electronics board.

Note that contact points 220 of FIG. 6 include 144 discrete points. This arrangement of contact points can be the result of a 12×12 contact point array, or can be representative of spatial sampling using a smaller number of discrete points. Thus, calibration circuit board 100 as described in FIGS. 2 and 3 can be used to derive Table 1 by repeatedly bringing the calibration circuit board into contact with a solder source, recording the status of each of contact points 120, moving to a new location, and so forth.

Figure 7:
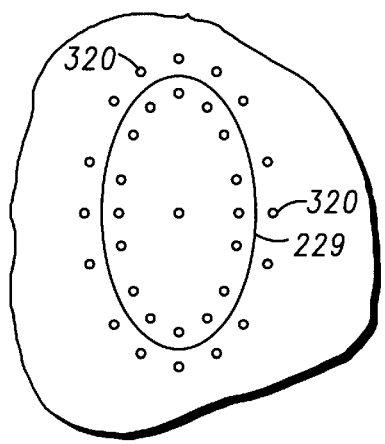
FIG. 7 is an isometric view of another calibration circuit board used in a method and system for characterizing a selective soldering process in accordance with a preferred embodiment of the invention.

FIG. 7 is an isometric view of another calibration circuit board used in a method and system for characterizing a selective soldering process in accordance with a preferred embodiment of the invention. In FIG. 7, the boundary of solder contact area 229 is straddled by at least two of contact points 320 which have been arranged on a dedicated circuit board similar to calibration circuit board 100 of FIGS. 2 and 3. Desirably, the calibration circuit board of FIG. 7 is used to periodically confirm the boundary of solder contact area 229. In this scenario, the calibration circuit board of FIG. 7 is brought into contact with a solder wave similar to solder wave 25 of FIG. 1, thereby allowing a computer unit, such as desktop computer unit 160 of FIG. 4, to determine which of contact points 320 couple with the solder wave. This procedure is then periodically repeated (perhaps during scheduled maintenance intervals) in order determine if solder contact area 229 has changed since a previous, similar measurement was conducted. Through the periodic application of this procedure, an accurate representation of solder contact area 229 can quickly be determined and compared with previous, similar measurements.

In an alternate embodiment, aspects of the invention may be practiced using optical means. In such an embodiment, a camera can be mounted above a transparent calibration circuit board and used to provide an optical record of the solder contact area. Thus, each of contact points 120 of FIGS. 2 and 3 is equivalent to a pixel, subpixel, or any other optical signal which can be used to assemble an image. These optical signals, which represent the solder contact area, are then processed by a computer unit and associated with a variety of selective soldering machine parameters such as those disclosed herein. This alternate embodiment can be advantageous since the resolution which can be achieved by optical means may be much greater than that which is possible using the contact points of FIGS. 2 and 3.

In conclusion, a method and system for selective soldering process characterization provides a technique for more tightly controlling the selective soldering process performed by a selective soldering machine. When deployed in a high-volume manufacturing environment, the use of the method and system provide a means for reducing the number of defects caused by improper soldering as well as increasing yield of electronic circuit boards produced by way of a selective soldering machine.

Accordingly, it is intended by the appended claims to cover all modifications of the invention that fall within the true spirit and scope of the invention.

What is claimed is:

1. A calibration circuit board for use with a system for characterizing an automated soldering process, comprising:
   a predominantly planar insulating material having substantial rigidity; and
   an arrangement of contact points distributed along a surface of said insulating material, each of said contact points being coupled to a optoisolator unit which supplies a potential to each of said contact points, said contact points being constructed using a substantially non-solderable material, and wherein said contact points of said calibration circuit board and said optoisolator unit characterize said automated soldering process.

2. The calibration circuit board of claim 1, wherein said substantially non-solderable material is nickel.

3. The calibration circuit board of claim 1, wherein said substantially non-solderable material is molybednum.

4. The calibration circuit board of claim 1, wherein said contact points are distributed at regular intervals in a region of said predominantly planar insulating material.

5. The calibration circuit board of claim 4, wherein said contact points are distributed in a pattern which substantially resembles a grid.

6. The calibration circuit board of claim 4, wherein said contact points are distributed in a pattern which substantially resembles a crosshair.

7. The calibration circuit board of claim 4, wherein each of said contact points includes a conductive annular ring which surrounds a conductor, said conductor conveying said potential from said optoisolator unit.

8. The calibration circuit board of claim 4, wherein each of said contact points includes a solid conductive pad which surrounds a conductor, said conductor conveying said potential from said optoisolator unit.

9. The calibration circuit board of claim 1, wherein said predominantly planar insulating material is a ceramic material.

10. The calibration circuit board of claim 1, wherein said predominantly planar insulating material is FR-4.

11. The calibration circuit board of claim 1 additionally comprising a trigger area which lies on at least one side of said arrangement of dontact points.

12. A calibration circuit board for use with a system for characterizing a selective soldering process, comprising:
    a predominantly planar conductive material having substantial rigidity; and
    an arrangement of contact points distributed along a surface of said predominantly planar conductive material, said contact points being constructed using an insulating sleeve which surrounds a substantially non-solderable conductive material, each of said contact points being coupled to a optoisolator unit which supplies a potential to each of said contact points, and wherein said contact points of said calibration circuit board and said optoisolator unit characterize said selective soldering process.

13. The calibration circuit board of claim 12, wherein said contact points are distributed at regular intervals in a region of said predominantly planar conductive material.

14. The calibration circuit board of claim 13, wherein said contact points are distributed in a pattern which substantially resembles a rectangular grid.

15. The calibration circuit board of claim 13, wherein said contact points are distributed in a pattern which substantially resembles a crosshair.

* * * * *